United States Patent [19]

Pettit

[11] 4,414,205

[45] Nov. 8, 1983

[54] CELL GROWTH INHIBITORY SUBSTANCES

[75] Inventor: George R. Pettit, Paradise Valley, Ariz.

[73] Assignee: University Patents, Inc., Tempe, Ariz.

[21] Appl. No.: 297,473

[22] Filed: Aug. 28, 1981

[51] Int. Cl.³ .................... A61K 37/00; A61K 35/56; C07G 7/00

[52] U.S. Cl. .................................... 424/177; 424/95; 260/112 R

[58] Field of Search .............. 424/95, 177; 260/112 R

[56] References Cited

PUBLICATIONS

Pettit et al.–J. of Natural Products vol. 44, No. 4, (1981), pp. 482–485.

Pettit et al.–Chem. Abst. vol. 95, (1981), p. 180,829V.

Makino–Chem. Abst. vol. 77, (1972), p. 98035C.

Eales, N. B., L.M.B.C. Memoirs, vol. XXIV, Proc. and Transactions of the Liverpool Biological Society, vol. XXXV, Session 1920–1921, "Typical British Marine Plants and Animals" in Aplysia, pp. 183–279.

Primary Examiner—Sam Rosen
Attorney, Agent, or Firm—Roman Saliwanchik

[57] ABSTRACT

Potent cell growth inhibitory substances have been obtained from the Indian Ocean sea hare Dolabella. These substances have been given the names dolastatin 1, dolastatin 2, and dolastatin 3. These compounds are characterized by physical and chemical parameters. Their utility as antiviral agents is supported by the disclosure of various preparations for such use.

10 Claims, 1 Drawing Figure

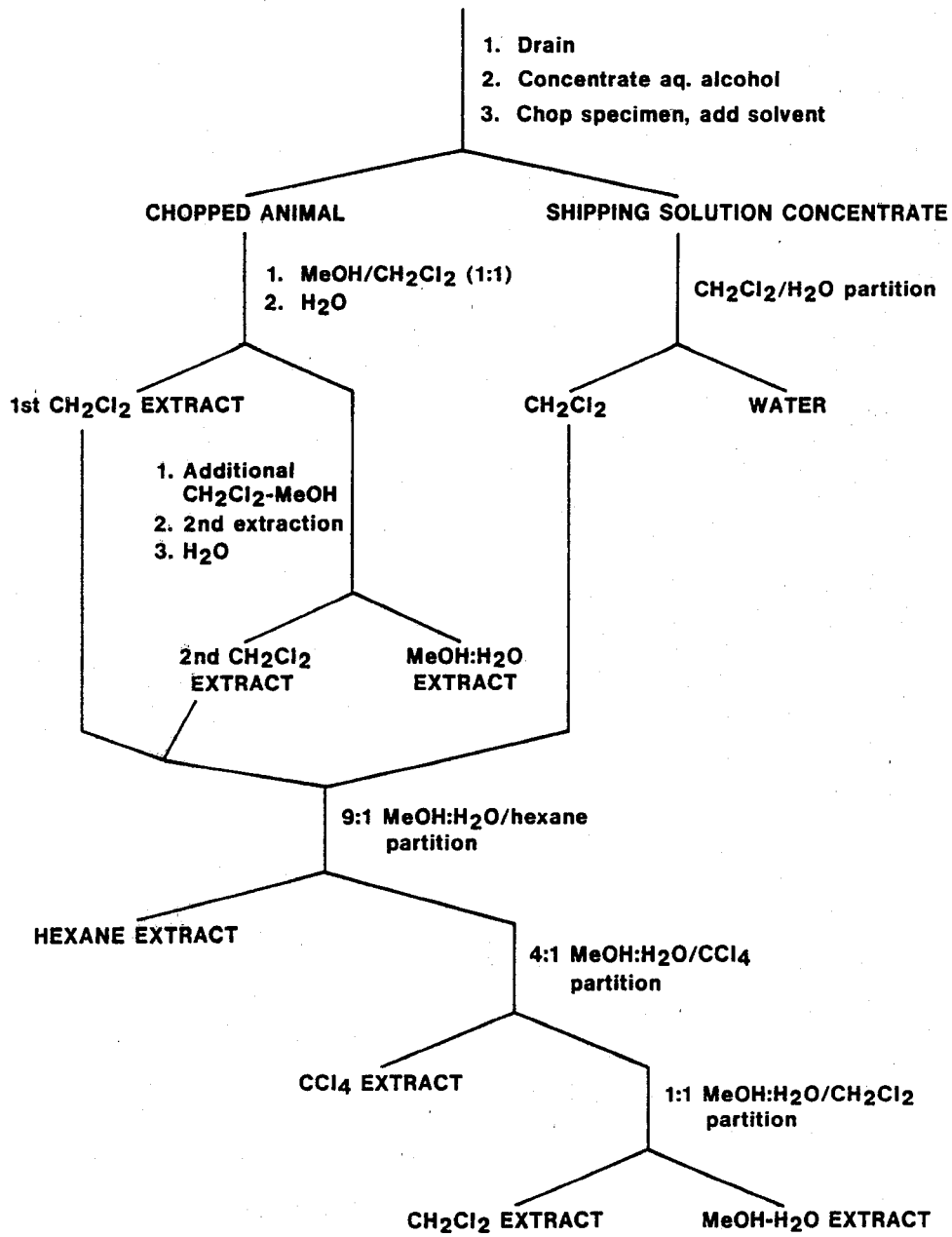

CELL GROWTH INHIBITORY SUBSTANCES

Financial assistance was provided by the National Cancer Institute (performed pursuant to contracts NO1-CM-12308, 67048 and 97262 with the Division of Cancer Treatment, NCI, National Institutes of Health, DHW) and grant numbers CA-16049-01 through 06 awarded by the National Cancer Institute, DHW, thus, the U.S. government has rights in this invention pursuant to the above-listed grants.

BRIEF SUMMARY OF THE INVENTION

Potent cell growth inhibitory substances designated dolastatins 1 thru 3 extracted from the Indian Ocean sea hare Dolabella. The first member of this new series, dolastatin 1, may represent the most potent anticancer agent so far uncovered with a 30% curative response using an intraperitoneal dose of 11 µg/kg in the National Cancer Institute's murine B16 melanoma test.

BACKGROUND OF THE INVENTION

The great Roman natural scientist Gaius Plinius Secundus (Pliny the Elder) in his comprehensive study of about 60 A.D. first described a most potent Indian Ocean sea hare of the genus Dolabella. [The Romans first designated Mollusca of the family Aplysidae as sea hares due to a similarity between the ears of a hare and the auriculate tentacles of these gastropods. Consult article by N. B. Eales, *L.M.B.C. Memoirs,* Vol. XXIV. on "Typical British Marine Plants and Animals," in Aplysia, edited by W. A. Hardman and J. Johnstone, (Liverpool University Press, 1921)]. Extracts from this animal and two related Aplysia species from the Mediterranean were well known for their toxic properties during the reign of Nero [Pliny, *Historia Naturalis,* Lib. IX., Lib. XXXII, ca. 60 A.D. and N. B. Eales, supra]. By 150 A.D. Nicander [N. B. Eales, supra] recognized the possibility of using such extracts for treatment of certain diseases. However, the potential of the Indian Ocean Dolabella with respect to modern medical problems was not recognized until the subject invention wherein extremely active anticancer constituents are isolated from the Indian Ocean *Dolabella auricularia* [The *D. auricularia* was probably the first described by Pliny and the minor variations recorded in subsequent literature as e.g., *D. andersonii, D. californica, D. ecaudata,* and *D. scapula* are actually one species, namely *D. auricularia,* see H. Engel, *Zool. Med. Museum Leiden,* 24, (1945)].

The dolastatins may correspond to the potent *D. auricularia* constituents recognized from ancient to fairly recent times [1969 Ph.D. dissertation of M. Watson, U. of Hawaii, "Some Aspects of the Pharmacology, Chemistry and Biology of the Midgut Gland Toxins of Some Hawaiian Sea Hares, especially *Dolabella auricularia* and *Aplysia pulmonica,*" University Microfilms Inc., Ann Arbor, Michigan]. Since dolastatin 1 has been shown by the U.S. National Cancer Institute to cause an 88% life extension with the murine P388 lymphocytic leukemia, and a 30% curative response against the murine B16 melanoma at intraperitoneal doses of 11 µg/kg/day, it may represent the most active (lowest dose) presently known antineoplastic agent.

DETAILED DESCRIPTION OF THE INVENTION

The Organism

Taxonomy:

Dolabella species belong to the family Aplysidae, the class Gastropoda and the phylum Mollusca. In a reference by H. Engel in "Zoologische Mededeelingen," Leiden, 24, 197-239 (1945), there are numerous color plates of specimens of Dolabella. Also in this reference is a listing of previously presumed different species of Dolabella which the author finds to be the same and identified as *Dolabella auricularia*. These species are: *Dolabella agassizi, D. andersonii, D. auricularia, D. callosa, D. dolabella, D. ecaudata, D. hasseltii, D. hemprichii, D. neira, D. peronii, D. rumphii, D. teremidi, D. tongana, D. truncata, D. variegata,* and *D. scapula*.

In appearance, the Dolabella used were olive green in color with a pear-shaped body and average length, 15–20 cm. The reference by H. Engel has detailed descriptions of Dolabella collected around the world.

The Dolabella collection site used for initial isolation of the dolastatins was on the eastern side of Mauritius in the Indian Ocean, approximate location, 21° S latitude, 56° E longitude, in 4–5 ft. deep water off the coast of the island.

Anotheer site where Dolabella can be collected is near Negros Island in the Philippines, approximate location 9° N latitude, 123° E longitude. Extracts of Dolabella species from five separate collections all contained antineoplastic activity.

Isolation and Purification of Dolastatins

A variety of methods can be used to isolate and purify the dolastatins from samples of the sea hare, for example, solvent extraction, partition chromatography, silica gel chromatography, liquid-liquid distribution in a Craig apparatus, adsorption on resins, and crystallization from solvents.

The following examples describe preferred processes, but are not to be construed as limiting.

EXAMPLE 1

Extraction

The shipping solution is drained from 45 gallons of marine material and the animals are ground (commercial meat grinder) and allowed to soak (ambient temperature) for at least 5 days in ethanol in 5-gallon pails. Four extractions are completed; the combined extracts are concentrated to an aqueous slurry. The first ethanol extract, designated F004, had cytotoxic activity with a 50% effective dose (ED$_{50}$) of $4.2 \times 10^{-2}$ µg/ml vs. P388 leukemia cells. The animal material is extracted twice with hot ethanol (modified Soxhlet apparatus) and the combined extract is also concentrated to an aqueous slurry. The three ethanol extracts, namely the shipping solution and both the ambient and hot ethanol extracts are partitioned separately. Work with the ambient extract follows in Example 2.

EXAMPLE 2

Solvent Partitioning

Aliquots (from 500 to 1000 ml) of the total aqueous slurry are transferred to 6-liter separatory funnels, diluted with water to a volume of about 3 liters, and extracted 5-6 times with methylene chloride (2 liters each). The total methylene chloride extract is 207.8 g of a dark greenish brown oil.

About 100 g of the total methylene chloride extract is used per 6-liter separatory funnel for the hexane-methanol:water (9:1) partition. Hexane (1.5 liters) is used to transfer the extract to the funnel, the resulting hexane solution is extracted with 9:1 methanol:water (4×1-liter). The combined methanol:water extract is reextracted with hexane (4×1.5 liters). The combined hexane extract is evaporated to dryness to yield 143.7 g.

The final step requires dilution of the methanol:water (9:1) to a 1:1 ratio. In 1-liter portions per 6-liter separatory funnel, the aqueous methanol is adjusted to a 1:1 ratio by adding water and is extracted 8-10 times with 2-liter amounts of methylene chloride to give a final combined extract weight of 57.0 g. This extract was designated F009. It had an $ED_{50}$ of $6.2\times10^{-2}$ μg/ml vs P388 leukemia.

EXAMPLE 3

Sephadex LH-20 Chromatography

The above methylene chloride extract (57.0 g) is divided among seven columns (3.8×244 cm) of LH-20 (about 700 g, dry) in methanol. Each column is loaded with extract in methanol (about 100 ml) and elution is allowed to proceed. After the chromatogram is complete, the fractions (20 ml per test tube, Gilson FC-220) are combined according to TLC comparisons (EtOAC:EtOH, 96.4 and $CHCl_3$:MeOH:$H_2O$, 90:10:0.8) by using iodine vapor, sulfuric acid (heated after spraying) and molybdatophosphoric acid (heated after spraying) as visualization reagents, on precoated silica gel plates (Uniplate, Analtech, Inc.). Active fractions, F106 (45.7 g) and F107 (4.65 g) corresponded to the combined analogous fractions from the seven columns.

The second chromatography step employs LH-20 with 4:1 methanol:methylene chloride as eluent. A method similar to that described above is used and the active material is concentrated in one fraction, F034 (32.1 g) with a P388 $ED_{50}$ of $1.1\times10^{-2}$ μg/ml.

EXAMPLE 4

Silica Gel Chromatography Using the Dry Column Method

A portion (about 2 g) of the active fraction (F034), obtained as described in Example 3, is chromatographed on silica gel using ethyl acetate and ethyl acetate:ethanol mixtures as solvent by the dry column technique. The active material is eluted by ethyl acetate:ethanol (97:3). Fractions are combined according to TLC comparison (ethyl acetate:ethanol, 96:4, and chloroform:methanol:water, 90:10:0.8). Visualization methods are the same as described above. The use of ceric sulfate solution (3% in 3 N sulfuric acid) is more effective than just sulfuric acid. Two active fractions, F052 (72.4 mg, P388 $ED_{50}$ $5.3\times10^{-4}$ μg/ml) and F053 (486.1 mg, P388 $ED_{50}$ $7.1\times10^{-3}$ μg/ml) are isolated from this column. The fraction F053 is rechromatographed by the same method to give two active fractions F071 (36.3 mg, P388 $ED_{50}$ $<10^{-4}$ μg/ml) and F072 (38.2 mg, P388 $ED_{50}$ $<10^{-4}$ μg/ml), respectively.

Chromatography of the remaining amount, about 27 g of F034, is performed as described above. The active fractions, F066 (0.744 g, P388 $ED_{50}$ $<10^{-4}$ μg/ml and F067 1.17 g, P388 $ED_{50}$ $<10^{-4}$ μg/ml) are eluted by ethyl acetate:ethanol (9:1) and (8:2).

For a third chromatography, the active fractions, F052, F071, F072, F066 and F067 (total weight, 2.06 g) are combined. The initial elution solvent is 97:3 ethyl acetate:ethanol and the most active fractions, F106-F111 are eluted by ethyl acetate:ethanol, 95:5 through 8:2. Each active fraction displays many components by TLC-UV (Mineral Light, UV 5.11, Ultra-Violet Products, Inc.) with some overlapping. Final purification employs either (or both) repetitive column separations (silica gel) or preparative TLC. For TLC evaluations, the system chloroform:methanol:water (90:10:0.8) is preferred.

EXAMPLE 5

Isolation of the Dolastatins

The active fractions F106-F111, are rechromatographed on silica gel using ethyl acetate:ethanol (97:3) and a wet chromatographic method. After TLC comparisons and combinations of analogous fractions, three fractions are found most active: F126 (39.0 mg, P388 $ED_{50}$ $3.3\times10^{-9}$ μg/ml), F127 (243.4 mg, P388 $ED_{50}$ $2.0\times10^{-9}$ μg/ml) and F128 (53.8 mg, P388 $ED_{50}$ $1.6\times10^{-9}$ μg/ml).

Separation of a portion of F127 (137.9 mg) is carried out using four low pressure columns in series. The sample is added to the first column (1×15 cm) which is in series with three prepacked columns (E. Merck; Size A); eluting solvent is chloroform:methanol:water, 97:3:0.2. A fraction from this chromatography (15.0 mg) is further separated on the same column series and solvent into fractions containing dolastatin 1, as evidenced by direct TLC comparison with the dolastatin 1 isolated previously.

Preparative TLC is performed using precoated plates (250μ) with chloroform:methanol:water, 90:10:0.8 as solvent. By aid of UV light, each dolastatin portion is collected and extracted with chloroform:methanol, 4:1, at least three times. These final separations provide the essentially pure dolastatins 1-3.

The drawing shows the scheme for the general extraction and solvent partitioning of marine animal constituents, as described in detail in the foregoing examples.

A description of the antitumor tests, described herein, appears in the reference by R. I. Geran, N. H. Greenberg, M. M. MacDonald, A. M. Schumacher and B. J. Abbott, *Cancer Chemother. Rep.* Part 3, Vol. 3(2): 1-103 (1972).

Physical Data for Dolastatins 1 through 3.
Physical Data for Dolastatin-1
Appearance—amorphous solid precipitated from $CHCl_3$-MeOH, $CH_2Cl_2$-EtOH or AcOEt-EtOH
Melting point—105°-111° C.
Thin layer chromatography (spots visualized by UV light or $I_2$ vapor. $I_2$ spots are yellow.)

| Solvent system | Rf |
|---|---|
| (AcOEt/EtOH 96:4) | 0.41 |
| ($CHCl_3$/EtOH 95:5) | 0.23 |
| ($CHCl_3$/MeOH/$H_2O$ 90:10:0.8) | 0.46 |

Ultraviolet spectrum
λMeOH/max 218.8, 230(sh) and 243(sh)nM.
Mass spectrum (Field desorption)
MW=991±1
+Ion±1: 1038 (M+2Na-H)+ 1014 (M+Na)+, 807, 668, 551, 100
+Ion±2: 783, 680, 409, 381.
Proton magnetic resonance "CDCl₃" (0.8% solution in CDCl₃)-60 MHz δ:0.90 (s), 0.99 (large peak), 1.05 (s), 1.10 (s), 1.18 (s), 1.26 (s), 1.80 (m), 2.06 (m), 2.17 (s), 2.28 (s, large peak), 2.44 (m), 3.03 (s), 3.16 (s), 3.34 (s, large peak), 3.38 (broad s), 3.90 (m), 4.12 (m), 4.80 (m), 5.57 (m), 6.91 (m), 7.22 (s, large peak), 7.26 (s), 7.73 (d, J=3.5 Hz).

"Acetone-d₆" (0.8% solution in acetone d₆)-60 MHz

δ:0.82 (s), 0.94 (m, large peak), 1.15 (m), 1.23 (s), 1.70 (m), 2.28 (s, large peak), 2.48 (m), 3.10 (s), 3.22 (s), 3.30 (s), 3.34 (s), 3.45 (m), 3.58 (m), 3.92 (m), 4.15, 4.81 (m), 5.69 (t). CDCl₃-90 MHz δ: 0.89 (s), 0.96 (s), 0.99 (s), 1.06 (s), 1.10 (s), 1.18 (s), 1.26 (s, large peak), 1.42 (s), 1.66 (broad s, large), 1.98 (s), 2.06 (s), 2.30 (broad s, large), 2.42 (s), 3.03 (s), 3.16 (s), 3.33 (s, large peak), 3.38 (s), 3.72 (s), 3.90 (m), 4.12 (m), 4.80 (q. J=2.5 Hz and J=5.0 Hz), 5.30 (s), 5.57 (q. J=2.5 Hz and 7.5 Hz), 6.91 (m), 7.22 (s), 7.26 (s, large peak), 7.74 (d., J=3.5 Hz).

Physical Data for Dolastatin-2

Appearance—amorphous solid precipitated from CHCl₃-MeOH, CH₂Cl₂-EtOH or AcOEt-EtOH.

Melting point—118°-121° C.

Thin layer chromatography (spots visualized by UV light or I₂ vapor. I₂ spots are yellow).

| Solvent system | Rf |
|---|---|
| (AcOEt/EtOH 95:5) | 0.24 |
| (CHCl₃/MeOH/H₂O 90:10:0.8) | 0.37 |

Ultraviolet spectrum

γMeOH/max 217.0, 232.0 (sh) and 270.0 (sh) nM.

Infrared spectrum—KBr 3400 (OH), 3060, 3040 (CH), 1740, 1641 (strong), 1455, 1410, 1390, 1262, 1210, 1190, 1097, 805 and 710 cm⁻¹.

Proton magnetic resonance

"CDCl₃" (0.5% Solution in CDCl₃)-60 MHz

δ:0.98 (broad s), 1.19 (m), 1.26 (s), 1.75 (m), 2.10 (m), 2.37 (m), 2.47 (m), 3.04 (s), 3.34 (s), 3.38 (broad s), 4.13 (m), 4.78 (m), 5.57 (m), 7.22 (s), 7.26 (s), 7.73 (m). "Acetone-d₆" (0.5% solution in Acetone-d₆)-60 MHz δ:0.89(s), 0.94 (s, large peak), 0.96 (s, large peak), 1.02 (s, large peak), 1.14 (m), 1.30 (s), 1.71 (m), 2.39 (s), 2.40 (s), 2.48 (m), 3.10 (s), 3.22 (s), 3.31 (s), 3.46 (m), 3.59 (m), 3.92 (m), 4.19 (m), 4.82 (m), 5.70 (m), 7.32 (m, large peak), 7.51 (q), 7.76 (t. J=3.2 Hz), 8.03 (6).

Amino Acid Analysis

Hydrolysis by: 6 N-HCl aq. for 24 hrs at 105°±5°, in sealed tube.

First time: Proline (5.21%), Glycine (0.26%), Alanine (0.85%), Valine (0.96%, Isoleucine (0.54%), and glutamic Acid (trace). Second time: Proline (6.56%), Glycine (1.12%), Alanine (2.71%), Valine (2.59%), Isoleucine (3.87%) and glutamic acid (1.2%).

Physical Data for Dolastatin-3

Appearance-amorphous solid precipitated from CHCl₃-MeOH, CH₃Cl₂-MeOH and AcOEt-EtOH Melting Point-133°-137° C.

Optical Rotation

[α]_D^{26° C.} (methanol) pf a 0.09% solution= −35.5°

Thin layer chromatography (Spots were visualized by UV light, I₂ vapor or ninhydrin spray. I₂ spots were yellow, ninhydrin spots were slight yellow.)

| Solvent System | R_f |
|---|---|
| (CHCl₃:MeOH:H₂O 90:10:0.8) | 0.30 ± 0.03 |
| (EtOAc:EtOH 96:4) | 0.27 ± 0.03 |

Ultraviolet spectrum

λMeOH/max 206 nm (ε 13,940) and 238 nm (ε 8,960).

NOTE: λmax 206 nm was corresponded to K-Band of the thiazole derivatives and λmax 238 nm was to B-Band of that. (See "Spectrometric Identification of Organic Compounds" by R. M. Silverstein and (G. C. Bassler, 1963, John Wiley & Sons, Inc., New York).

Infrared spectrum-KBr peaks at: 3427, 3379 (s), 3330 (shoulder)(NH), 3090 (w)(NH), 3020 (w)(NH), 1670 (s)(-CONH-), 1629 (s)(-CONH-), 1544 (s)(-CONH-), 1501 (m), 1494 (w), 1445 (s) (thiazole group), 1390 (w), 1370 (w), 1310 (w), 1240 (m) (thiazole goup), 1065 (w) (thiazole group), 823 (w), 760 (w) and 620 (m) cm⁻¹.

NOTE: The thiazoles have each band in the ranges 1570-1395, 1420-1260 and 1140-940 cm⁻¹. [See "Advances in Infrared Group Frequencies" by L. J. Bellamy, p. 214, 1968, Methuen & Co. Ltd. or Rao and Venkataraghavan, Spectrochim. Acta., 1962, 18, 541. Original literature: Thorn, Can. J. Chem. 38, 1439, 2349 (1960).]

Mass spectrum

Field desorption: 661 (M+H)

Electron impact: 660.2771 (M), 632.2554 (M-CO), 562.1992 (-Pro+H), 450.1175 (-Leu), 422.1177 (-CO,-Leu), 351.0789 (-Val), 322.0230, 310.1306, 281.1876 (Pro-Leu-Val-(O), 213.1621 (Val.Leu+H), 210.1351 (Pro-Leu).

Proton magnetic resonance (Bruker WH-90 NMR spectrometer)

CDCl₃—90MHz 8.72(1H,d,J = 5.0Hz, NH), 8.31(1H,d,J = 9.0Hz; NH), 7.85

(1H,d,J = 8.5Hz, NH), 8.09(1H,S, 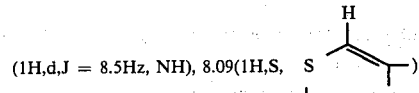)

8.07(1H,S, 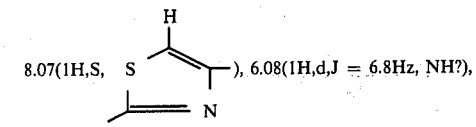), 6.08(1H,d,J = 6.8Hz, NH?), 5.49(2H,m,NH₂?), 5.36(1H,d,J = 7.0Hz ⟶H), 5.16(1H,d,J = 7.0Hz), ⟶H), 4.75(2H,t, or q J = 8.8Hz, —CH₂—), 4.54(1H,d,J = 1.8Hz), 4.04-3.49 (ca. 4H, m, H), 2.5-1.8 (ca. 16~18H, m(big peak), CH₂), 1.20(3H,d,J = 3.9Hz 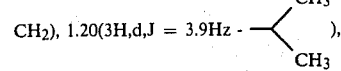), 1.10(3H,d, 3.9Hz, 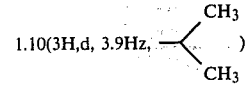)

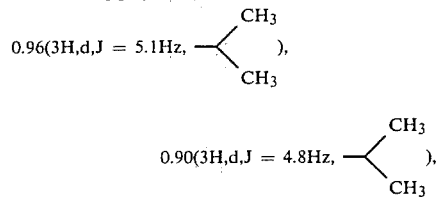

0.96(3H,d,J = 5.1Hz, CH₃/CH₃ ), 0.90(3H,d,J = 4.8Hz, CH₃/CH₃ ), $^{13}$C Nuclear magnetic resonance δ(ppm): 174.8 (s,c=o), 171.9 (s, Leu c=o), 171.2 (s, c=o), 171.1 (s, Val c=o), 169.5 (s, Pro c=o), 165.8 (s, c=o or c=N), 161.0 (s, c=N or c=o), 160.2 (s, c=N or c=o), 149.1 (s, >C=C or >c=N), 148.3 (s, >c=c or >c=N), 124.4 (d, >c=c-H), 123.8 (d, >c=c-H), 62.6 (d, α-position of proline group), 55.7 (d, α-position of Valine group), 55.0 (d, -C-N-?), 48.6 (d, α-position of Leucine group), 48.3 (t, δ-position of Proline group), 41.0 (t, β-position of Leucine group), 37.7, 33.3 (d), 31.8 (d, β-position of Valine group), 29.7 (t, β-position of Proline group), 28.4, 25.5 (t, α-position of Proline group and Leucine group), 23.3 (q, δ-position of leucine group), 21.2 (q, δ-position of Leucine group), 19.6 (q, α-position of Valine group), 18.6 (q, α-position of Valine group).

Signals (s, d, t, and q) were obtained by off-resonance.

Amino acid analysis (Auto Amino Acid Analyser-Beckman Model 121)

Hydrolysis by 6.1 N HCl aq. at 105° C.±5° C. for 24 hours in a sealed tube.

First Time: Proline (4.72%), valine (4.87%), leucine (5.45%).

Second Time: Proline 5.75%, valine (4.55%), leucine (7.36%).

Notes:

(a) In each case two unknown compounds were detected;

(b) Composition of proline, valine and leucine could be the 1:1:1 Ratio.

Elemental Analysis

| Calcd. | (a) | (b) | (c) | (d) |
| --- | --- | --- | --- | --- |
| C | 52.71% | 51.83% | 56.90% | 60.26% |
| H | 6.10% | 6.54% | 6.44% | 8.91% |
| N | 16.96% | 12.78% | 12.21% | 12.85% |
| O | 14.53% | | | |
| S | 9.70% | 10.48% | 3.10% | |

(a) by Galbraith Lab. Inc. (Tennessee).
(b) by Barnhardt.
(c) by Spang.
(d) by Analytische Laborator. (German).

Empirical Formula $C_{29}H_{40}N_8O_6S_2$
(M.W. 660.2771)

Antineoplastic Activity of Dolastatins

| | Mouse Tumor System | | | |
| --- | --- | --- | --- | --- |
| | B₁₆ melanoma[a] | | P₃₈₈ leukemia[a] | |
| Compound | optimal dose in μg/kg/ injection[b] | life span in percent of controls[c] | optimal dose in μg/kg/ injection[b] | life span in percent of controls[c] |
| Dolastatin 1 | 11 | 240(3/10) | 11 | 188 |
| Dolastatin 2 | 25 | 161 | 27 | 166 |
| Dolastatin 3 | 100 | 99 | 50 | 178 |

[a]tumors were inoculated intraperitoneally (i.p.)
[b]compounds were administered i.p. everyday for 9 days starting on the first day after tumor inoculation.
[c]Calculated from median survival times; Nos. in parentheses = No. of cures/total No. of mice in group. Cured mice survive for at least 60 days.

The administration of dolastatins is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease, the type of host involved, its age, health, weight, kind of concurrent treatment, if any, frequency of treatment and therapeutic ratio.

Illustratively, dosage levels of the administered active ingredients can be: intravenous, 0.1 to about 200 μg/kg; intraperitoneal, 1 to about 1000 μg/kg; subcutaneous, 1 to about 1000 μg/kg; intramuscular, 1 to about 1000 μg/kg; orally, 0.01 to about 10 mg/kg; intranasal instillation, 0.01 to about 10 mg/kg; and aerosol, 0.01 to about 20 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition, and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as in adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal installation, fluid unit dosage forms are prepared utilizing an active ingredient and a suitable pharmaceutical vehicle, water being preferred, or by dry powder for insufflation.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carried or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material or therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral or antineoplastic agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

COMPOSITION EXAMPLE 1

Hard-Gelatin Capsules

One thousand two-piece hard gelatin capsules for oral use, each capsule containing 10 mg of a dolastatin, are prepared from the following types and amounts of ingredients:

| a dolastatin, micronized | 10 gm |
|---|---|
| Lactose | 190 gm |
| Corn Starch | 20 gm |
| Talc | 20 gm |
| Magnesium stearate | 2 gm |

The dolastatin finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a dolastatin in 5, 25 and 50 mg amounts by substituting 5 gm, 25 gm and 50 gm of a dolastatin for the 100 gm used above.

COMPOSITION EXAMPLE 2

Soft Gelatin Capsules

One-piece soft gelatin capsules for oral use, each containing 250 mg of a dolastatin (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION EXAMPLE 3

Tablets

One thousand tablets, each containing 50 mg of a dolastatin are prepared from the following types and amounts of ingredients:

| A dolastatin, micronized | 50 gm |
|---|---|
| Lactose | 525 gm |
| Corn starch | 50 gm |
| Magnesium stearate | 4 gm |
| Light liquid petrolatum | 5 gm |

The dolastatin finely divided by means of an air micronizer, is added to the other ingredients and then thoroughly mixed and slugged. The slugs are broken down by forcing through a Number Sixteen screen. The resulting granules are then compressed into tablets, each tablet containing 50 mg of the dolastatin.

The foregoing tablets are useful for treating a neoplastic disease by the oral administration of one or two tablets one to four times a day.

Using the procedure above, tablets are similarly prepared containing a dolastatin in 25 mg and 10 mg amounts by substituting 25 gm and 1 gm of a dolastatin for the 50 gm used above.

COMPOSITION EXAMPLE 4

Oral Suspension

One thousand ml of an aqueous suspension for oral use, containing in each taspoonful (5 ml) dose, 50 mg of a dolastatin, is prepared from the following types and amounts of ingredients:

| A dolastatin, micronized | 10 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The dolastatin, finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION EXAMPLE 5

A sterile aqueous suspension for parenteral injection, containing in 1 ml 300 mg of a dolastatin for treating a neoplastic disease, is prepared from the following types and amounts of ingredients:

| A dolastatin, micronized | 30 gm |
|---|---|
| Polysorbate 80 | 5 gm |
| Methylparaben | 2.5 gm |
| Propylparaben | 0.17 gm |
| Water for injection, q.s. 1000 ml. | |

All the ingredients, except the dolastatin, are dissolved in the water and the solution sterilized by filtration. To the sterile solution is added the sterilized dolastatin, finely divided by means of an air micronizer, and the final suspension is filled into sterile vials and the vials sealed.

The composition so prepared is useful for treating a neoplastic disease at a dose of 1 milliliter (1 M) three times a day.

COMPOSITION EXAMPLE 6

Suppository, Rectal and Vaginal

One thousand suppositories, each weighing 2.5 gm and containing 15 mg of a dolastatin are prepared from the following types and amounts of ingredients:

| A dolastatin, micronized | 15 gm |
|---|---|
| Propylene glycol | 150 gm |
| Polyethylene glycol #4000, q.s. | 2,500 gm |

The dolastatin is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION EXAMPLE 7

Intranasal Suspension

One thousand ml of a sterile aqueous suspension for intranasal instillation, containing in each ml 15 mg of a dolastatin, is prepared from the following types and amounts of ingredients:

| A dolastatin, micronized | 15 gm |
|---|---|
| Polysorbate 80 | 5 gm |
| Methylparaben | 2.5 gm |
| Propylparaben | 0.17 gm |
| Deionized water, q.s. 1000 ml. | |

All the ingredients, except the dolastatin, are dissolved in the water and the solution sterilized by filtration. To the sterile solution is added the sterilized dolastatin, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present, as shown in Examples 12-14 in the undiluted pure form for use locally about the cutis, intranasally, pharyngolaryngeally, bronchially, broncholially or orally.

COMPOSITION EXAMPLE 8

Powder

Five grams of a dolastatin in bulk form is finely divided by means of an air micronizer. The micronized powder is placed in a shaker-type container.

The foregoing composition is useful for treating a neoplastic disease, at localized sites by applying the powder one to four times per day.

COMPOSITION EXAMPLE 9

Oral Powder

Electron impact: 660.2771 (M), 632.2554 (M-CO), 562.1992 (-Pro+H), 450.1175 (-Leu), 422.1177 (-CO,-Leu), 351.0789 (-Val), 322.0230, 310.1306, 281.1876 (Pro-Leu-Val-(O), 213.1621 (Val.-Leu+H), 210.1351 (Pro-Leu);

Amino acid analysis

Hydrolysis by 6.1 N HCl aq. at 105° C.±5° C. for 24 hours in a sealed tube;

First Time: Proline (4.72%), valine (4.87%), leucine (5.45%);

Second Time: Proline 5.75%, valine (4.55%), leucine (7.36%);

| Elemental Analysis | | | | |
|---|---|---|---|---|
| Calcd. | (a) | (b) | (c) | (d) |
| C | 52.71% | 51.83% | 56.90% | 60.26% |
| H | 6.10% | 6.54% | 6.44% | 8.91% |
| N | 16.96% | 12.78% | 12.21% | 12.85% |
| O | 14.53% | | | |
| S | 9.70% | 10.48% | 3.10%; | |

Empirical Formula
$C_{29}H_{40}N_8O_6S_2$
(M.W. 660.809).

4. A process for treating an animal or human hosting a neoplastic disease which comprises the administration of an effective amount of dolastatin 1 to said host.

5. A process for treating an animal or human hosting a neoplastic disease which comprises the administration of an effective amount of dolastatin 2 to said host.

6. A process for treating an animal or human hosting a neoplastic disease which comprises the administration of an effective amount of dolastatin 3 to said host.

7. A process for preparing dolastatins active against P388 leukemia which comprises:
   (a) extracting a ground preparation of the Indian Ocean sea hare Dolabella with ethanol to obtain an ethanolic extract;
   (b) subjecting said ethanolic extract to solvent partitioning to obtain an extract showing activity against P388 leukemia;
   (c) chromatographing said active extract and isolating the fractions active against P388 leukemia; and,
   (d) rechromatographing said active fraction to obtain further fractions active against P388 leukemia.

8. A process for preparing dolastatin 1 which comprises chromatographing the final active fractions obtained in claim 7 on silica gel.

9. A process for preparing dolastatin 2 which comprises chromatographing the final active fractions obtained in claim 7 on silica gel.

10. A process for preparing dolastatin 3 which comprises chromatographing the final active fractions obtained in claim 7 or silica gel.

* * * * *